(12) United States Patent
Bersier et al.

(10) Patent No.: US 10,689,350 B1
(45) Date of Patent: Jun. 23, 2020

(54) METHOD FOR PREPARATION OF CHLORINATED S-PROPYLTHIOBARBITURIC ACID

(71) Applicant: LONZA LTD, Visp (CH)

(72) Inventors: Michael Bersier, Ausserberg (CH); Paul Hanselmann, Brig-Glis (CH); Candid Stoffel, Visperterminen (CH)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 16/621,222

(22) PCT Filed: Jul. 16, 2018

(86) PCT No.: PCT/EP2018/069193
§ 371 (c)(1),
(2) Date: Dec. 10, 2019

(87) PCT Pub. No.: WO2019/016111
PCT Pub. Date: Jan. 24, 2019

Related U.S. Application Data

(60) Provisional application No. 62/533,838, filed on Jul. 18, 2017.

(30) Foreign Application Priority Data

Jul. 18, 2017 (EP) .................... 17181961

(51) Int. Cl.
*C07D 239/47* (2006.01)
*C07D 239/30* (2006.01)

(52) U.S. Cl.
CPC ......... *C07D 239/47* (2013.01); *C07D 239/30* (2013.01)

(58) Field of Classification Search
CPC ........................... C07D 239/30; C07D 239/47
USPC .................................................. 544/315, 316
See application file for complete search history.

(56) References Cited

U.S. PATENT DOCUMENTS

2013/0030176 A1    1/2013   Khile et al.

FOREIGN PATENT DOCUMENTS

| WO | 9905142 A1 | 2/1999 |
| WO | 0200628 A2 | 1/2002 |
| WO | 2011017108 A2 | 2/2011 |
| WO | 2012085665 A2 | 6/2012 |

OTHER PUBLICATIONS

Du et al., "Synthesis, Antiplatelet Aggregation Activity Evaluation and 3D-QSAR of a Series of Novel 6-Alkylamino(Alkoxyl)-2-Propylthio-8-Azapurine Nucleosides", Journal of Heterocyclic Chemistry,vol. 54, No. 1, 2016, pp. 436-449.
International Search Report and Written Opinion issued in corresponding International Patent Application No. PCT/EP2018/069193 dated Sep. 10, 2018 (12 pages).

*Primary Examiner* — Deepak R Rao
(74) *Attorney, Agent, or Firm* — MH2 Technology Law Group, LLP

(57) ABSTRACT

The invention discloses a method for preparation of 4,6-dichloro-5-nitro-2-(propylthio)pyrimidine by conversion of 5-nitro-2-propylthiopyrimidine-4,6-diol with phosgene in the presence of DMF.

10 Claims, No Drawings

METHOD FOR PREPARATION OF CHLORINATED S-PROPYLTHIOBARBITURIC ACID

CROSS-REFERENCE TO RELATED APPLICATIONS

This application is a U.S. National Stage application of PCT/EP2018/069193 filed 16 Jul. 2018, which claims priority to U.S. Provisional Patent Application No. 62/533,838 filed 18 Jul. 2017, and European Patent Application No. 17181961.8 filed 18 Jul. 2017, the entire disclosures of which are hereby incorporated by reference in their entireties.

The invention discloses a method for preparation of 4,6-dichloro-5-nitro-2-(propylthio)pyrimidine by conversion of 5-nitro-2-propylthiopyrimidine-4,6-diol with phosgene in the presence of DMF.

BACKGROUND OF THE INVENTION

US 2013/0030176 A1 discloses of method for preparation of 4,6-dichloro-5-nitro-2-(propylthio)pyrimidine and its use as intermediate for the preparation of ticagrelor. Example 10 discloses a yield of 233.5 g of the 4,6-dichloro-5-nitro-2-(propylthio)pyrimidine (MW 266 g/mol) with a purity of 99.45% is disclosed; with a MW of 229 g/mol for the substrate 5-nitro-2-propylthiopyrimidine-4,6-diol and a starting amount of 200 g the yield is 99.9%, which is admittedly very high.

Nevertheless the method uses phosphorous oxychloride (MW 153 g/mol) as Cl source for the exchange of the OH residues against Cl. The given 425.6 g of phosphorous oxychloride are converted by the reaction ultimately to 271 g phosphoric acid $H_3PO_4$ (MW 100). So 1.16 times, of the weight of the product, of phosphoric acid needs to be disposed of. This waste is a serious environmental challenge as well as a cost factor.

There was a need for a process that does not pose the mentioned waste problem in form of $H_3PO_4$.

An extensive screening of phosgene as alternative Cl source without catalyst, with various catalysts and with various solvents was not successful but showing yields of not more than 32%, instead showing significant amounts of undesired by products, as documented herein under Comparative Examples 1 to 60. Only one combination, the combination of phosgene with DMF, surprisingly showed satisfying yields.

The method has the advantage of comparably high yields without the problem of generation of $H_3PO_4$ as waste.

The following abbreviations are used, if not otherwise stated:
compound of formula (1) 5-nitro-2-propylthiopyrimidine-4,6-diol, also called 5-nitro-2-propylsulfanyl-pyrimidine-4,6-diol
compound of formula (2) 4,6-dichloro-5-nitro-2-(propylthio)pyrimidine
DMF dimethyl formamide
eq equivalent
RT room temperature
MW molecular weight

SUMMARY OF THE INVENTION

Subject of the invention is a method for the preparation of compound of formula (2)

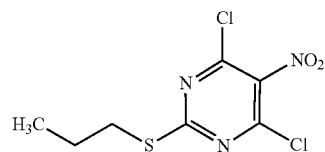

by a reaction REAC1 of compound of formula (1)

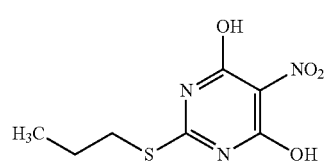

with a compound PHOS in the presence of DMF;
PHOS is selected from the group consisting of phosgene, diphosgene, triphosgene and mixtures thereof.

DETAILED DESCRIPTION OF THE INVENTION

Compound of formula (1) is a known compound and can be produced by known methods.
Preferably, PHOS is phosgene.
Preferably, the molar amount of PHOS is from 2 to 5 times, more preferably from 2 to 4 times, even more preferably from 2 to 3 times, of the molar amount of compound of formula (1).
Preferably, the amount of DMF is from 10 to 100 times, more preferably from 15 to 75 times, even more preferably from 15 to 50 times, especially from 15 to 40 times, more specially from 20 to 30 times, of the weight of PHOS.
Preferably, the reaction temperature TEMPI of REAC1 is from −10 to 50° C., more preferably from −5 to 40° C., even more preferably from −5 to 30° C., especially from −2.5 to 25° C.
Preferably, the reaction time TIME1 of REAC1 is from 5 h to 48 h, more preferably from 10 h to 24 h, even more preferably of from 12 h to 20 h.
In one embodiment, REAC1 is in the beginning of TIME1 done at a lower temperature than at the end of TIME1;
preferably, REAC1 is done at first for 4.5 h to 41 h at −10 to 9° C. and thereafter for 30 min to 7 h at 10 to 50° C.;
more preferably, REAC1 is done at first for 9 h to 21 h at −5 to 7° C. and thereafter for 1 h to 3 h at 12 to 40° C.;
even more preferably, REAC1 is done at first for 10.5 h to 19.5 h at −5 to 5° C. and thereafter for 1.5 h to 2.5 h at 15 to 30° C.;
Preferably, the DMF acts also as solvent in REAC1.
More preferably, compound of formula (1) is dissolved in DMF to provide a solution SOL-1, and PHOS is dissolved in DMF to provide a solution SOL-PHOS; and SOL-1 and SOL-PHOS are mixed with each other to provide for REAC1; preferably, for the mixing of SOL-1 with SOL-PHOS, SOL-1 is added to SOL-PHOS.
Therefore in one embodiment, the amount of DMF for preparation of SOL-1 is from 1 to 10 times, more preferably from 1.5 to 7.5 times, even more preferably from 2.5 to 7.5 times, of the weight of compound of formula (1); and the amount of DMF for preparation of SOL-PHOS is from 10 to 90 times, more preferably from 10 to 50 times, even more preferably from 15 to 40 times, especially from 15 to 30 times, of the weight of PHOS.

After REAC1, compound of formula (2) can be isolated and purified by conventional methods, which are known to those skilled in the art. These conventional methods include quenching the reaction mixture from REAC1 with water, with a solvent or with both water and a solvent, extraction, distillation, preferably fractional distillation, which can be done under reduced pressure, crystallization, chromatography, filtration, washing or any combination of these methods.

Preferably, the solvent that is used for quenching the reaction mixture is preferably an organic solvent, more preferably toluene; preferably, the quenching is done with water and toluene, thereby two phases are generated; then the phases are separated and the organic phase is evaporated to provide compound of formula (2).

Preferably, after REAC1 toluene and water is added to the reaction mixture.

Preferably, the amount of water is from 5 to 15 times, more preferably from 7.5 to 12.5 times, of the weight of compound of formula (1).

Preferably, the amount of toluene is from 4 to 14 times, more preferably from 6.5 to 11 times, of the weight of compound of formula (1).

Preferably, the addition of toluene and water is done at a temperature of from −10 to 30° C., more preferably of from −5 to 20° C., even more preferably of from −5 to 15° C., especially of from −5 to 10° C., more especially of from −5 to 5° C., even more especially of from −2.5 to 2.5° C.

EXAMPLES

Compound of Formula (3):

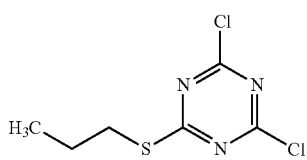

(3)

Compound of Formula (4):

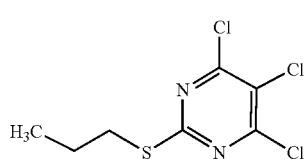

(4)

Compound of Formula (5):

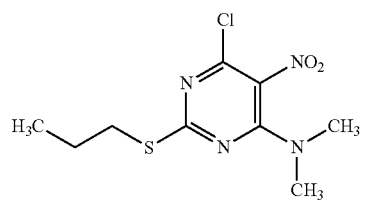

(5)

GC Method
Instrument:
Hewlett Packard gas chromatograph 6890 with a split injector and a flame ionisation detector or an instrument with corresponding performance and quality.
Column:
HP-1 (SIMDIST), 15 m×0.53 mm, 0.15 micrometer film-thickness, polydimethylsiloxane (or an equivalent column).
Instrument. Settings:

| OVEN: | |
|---|---|
| INITIAL TEMP | 50° C. |
| HOLD | 2 min |
| RAMP 1 | 20° C./min |
| NEXT TEMP | 320° C. |
| HOLD | 10 min |
| INJECTOR: | |
| Injection volume | 1 microliter |
| Check the auto-injector parameters. | |
| INLETS: | |
| INJ. MODE | Split |
| INJ TEMP | 250° C. |
| SPLIT FLOW | 200 ml/min |
| SPLIT RATIO | 25:1 |
| MODE | constant flow 8.0 ml/min |
| DETECTORS: | |
| DET TEMP | 300° C. |
| Check the FID gas flow rates. | |

The GC results are given in area %.

Comparative Examples 1 to 42—with Base 5.0 g (21.62 mmol, 1 eq) of compound of formula (1) were dissolved in 25 mL of solvent SOLV and base was added. 100 mL of SOLV were mixed with 4.7 g of phosgene (47.56 mmol. 2.2 eq) at 0° C. The solution of compound of formula (1) and base was added at 0° C. to the mixture of SOLV with phosgene. After stirring for 5 h at 0° C. and then for 2 h at RT, a sample from the reaction mixture was taken and analysed with GC. Result are shown in Table 1 with the following abbreviations:
CE Comparative Example
DPA-2.2 Diisopropylamine, 2.2 eq
DPA-2.5 Diisopropylamine, 2.5 eq
EMP-2.2 5-Ethyl-2-methylpyridine, 2.2 eq
NMM-2.2 N-Methylmorpholine, 2.2 eq
TEA-2.2 Triethylamine (2.2 eq.)
(2) compound of formula (2)
(3) compound of formula (2)
(4) compound of formula (4)

TABLE 1

| CE | Base | SOLV | GC Results (2) | (3) | (4) |
|---|---|---|---|---|---|
| 1 | DPA-2.2 | Dichloromethane | 20% | 15% | 10% |
| 2 | DPA-2.2 | Toluene | 25% | 12% | 8% |
| 3 | DPA-2.2 | Acetonitrile | 30% | 17% | 12% |
| 4 | DPA-2.2 | Chlorobenzene | 10% | 18% | 9% |
| 5 | DPA-2.2 | Sulfolane | 32% | 12% | 14% |
| 6 | DPA-2.2 | Dimethyl carbonate | 12% | 19% | 5% |
| 7 | DPA-2.5 | Dichloromethane | 20% | 15% | 10% |
| 8 | DPA-2.5 | Toluene | 25% | 12% | 8% |
| 9 | DPA-2.5 | Acetonitrile | 30% | 17% | 12% |
| 10 | DPA-2.5 | Chlorobenzene | 10% | 18% | 9% |
| 11 | DPA-2.5 | Sulfolane | 32% | 12% | 14% |
| 12 | DPA-2.5 | Dimethyl carbonate | 12% | 19% | 5% |
| 13 | 3-Picoline (2.2 eq.) | Dichloromethane | 21% | 18% | 11% |
| 14 | 3-Picoline (2.2 eq.) | Toluene | 28% | 13% | 8% |
| 15 | 3-Picoline (2.2 eq.) | Acetonitrile | 31% | 12% | 7% |
| 16 | 3-Picoline (2.2 eq.) | Chlorobenzene | 17% | 22% | 15% |
| 17 | 3-Picoline (2.2 eq.) | Sulfolane | 22% | 18% | 10% |
| 18 | 3-Picoline (2.2 eq.) | Dimethyl carbonate | 28% | 11% | 15% |
| 19 | TEA-2.2 | Dichloromethane | 20% | 14% | 8% |
| 20 | TEA-2.2 | Toluene | 25% | 12% | 8% |
| 21 | TEA-2.2 | Acetonitrile | 30% | 17% | 12% |
| 22 | TEA-2.2 | Chlorobenzene | 10% | 18% | 9% |
| 23 | TEA-2.2 | Sulfolane | 32% | 12% | 14% |
| 24 | TEA-2.2 | Dimethyl carbonate | 12% | 19% | 5% |
| 25 | Pyridine (2.2 eq.) | Dichloromethane | 20% | 15% | 10% |
| 26 | Pyridine (2.2 eq.) | Toluene | 25% | 12% | 8% |
| 27 | Pyridine (2.2 eq.) | Acetonitrile | 30% | 17% | 12% |
| 28 | Pyridine (2.2 eq.) | Chlorobenzene | 12% | 19% | 5% |
| 29 | Pyridine (2.2 eq.) | Sulfolane | 20% | 15% | 10% |
| 30 | Pyridine (2.2 eq.) | Dimethyl carbonate | 25% | 12% | 8% |
| 31 | EMP-2.2 | Dichloromethane | 30% | 17% | 12% |
| 32 | EMP-2.2 | Toluene | 10% | 18% | 9% |
| 33 | EMP-2.2 | Acetonitrile | 32% | 12% | 14% |
| 34 | EMP-2.2 | Chlorobenzene | 12% | 19% | 5% |
| 35 | EMP-2.2 | Sulfolane | 21% | 18% | 11% |
| 36 | EMP-2.2 | Dimethyl carbonate | 28% | 13% | 8% |
| 37 | NMM-2.2 | Dichloromethane | 16% | 15% | 8% |
| 38 | NMM-2.2 | Toluene | 20% | 15% | 15% |
| 39 | NMM-2.2 | Acetonitrile | 18% | 15% | 5% |
| 40 | NMM-2.2 | Chlorobenzene | 20% | 18% | 10% |
| 41 | NMM-2.2 | Sulfolane | 22% | 18% | 10% |
| 42 | NMM-2.2 | Dimethyl carbonate | 28% | 15% | 8% |

Comparative Examples 43 to 60—without Base 5.0 g (21.62 mmol, 1 eq) of compound of formula (1) were dissolved in 125 mL of solvent SOLV and Catalyst was added. 4.7 g of phosgene (47.56 mmol, 2.2 eq) were added at 0° C. After 5 h at 0° C., then 2 h at RT and then 2 h at 40° C., a sample from the reaction mixture was taken and analysed with GC.

Result are shown in Table 2 with the following abbreviations:
(2) compound of formula (2)
CE Comparative Example
TPP-0.1 Triphenylphosphine, 0.1 eq
TPP-0.3 Triphenylphosphine, 0.3 eq

TABLE 2

| CE | Catalyst | SOLV | Remarks |
|---|---|---|---|
| 43 | TPP-0.1 | Dichloromethane | less than 0.5% of (2) |
| 44 | TPP-0.1 | Toluene | less than 0.5% of (2) |
| 45 | TPP-0.1 | Acetonitrile | less than 0.5% of (2) |
| 46 | TPP-0.1 | Chlorobenzene | less than 0.5% of (2) |
| 47 | TPP-0.1 | Sulfolane | less than 0.5% of (2) |
| 48 | TPP-0.1 | Dimethyl carbonate | less than 0.5% of (2) |
| 49 | TPP-0.3 | Dichloromethane | less than 0.5% of (2) |
| 50 | TPP-0.3 | Toluene | less than 0.5% of (2) |
| 51 | TPP-0.3 | Acetonitrile | less than 0.5% of (2) |
| 52 | TPP-0.3 | Chlorobenzene | less than 0.5% of (2) |
| 53 | TPP-0.3 | Sulfo lane | less than 0.5% of (2) |
| 54 | TPP-0.3 | Dimethyl carbonate | less than 0.5% of (2) |
| 55 | no catalyst | Dichloromethane | less than 0.5% of (2) |
| 56 | no catalyst | Toluene | less than 0.5% of (2) |
| 57 | no catalyst | Acetonitrile | less than 0.5% of (2) |
| 58 | no catalyst | Chlorobenzene | less than 0.5% of (2) |
| 59 | no catalyst | Sulfolane | less than 0.5% of (2) |
| 60 | no catalyst | Dimethyl carbonate | less than 0.5% of 2 |

Example 1—with DMF 5.0 g (21.62 mmol, 1 eq) compound of formula (1) were dissolved in 25 mL of DMF. 100 mL of DMF were mixed with 4.7 g of phosgene (47.56 mmol, 2.2 eq) at 0° C. The solution of compound of formula (1) was added to the mixture of DMF with phosgene at 0° C. After 14 h stirring at 0° C. and then 2 h at RT, 50 mL of water and 50 mL of toluene were added at 0° C. The mixture was stirred 15 min and the phases were separated. The organic phase was evaporated under vacuum. 5 g of compound of formula (2) were isolated (83% yield, 98.2% purity, GC analysis showed 1.1% of compound of formula (3), 0.32% of compound of formula (4) and 0.35% of compound of formula (5)).

Example 2—with DMF 50 g (216.2 mmol, 1 eq) of compound of formula (1) were dissolved in 250 mL of DMF. 1000 mL of DMF were mixed with 47 g of phosgene (475.6 mmol, 2.2 eq) at 0° C. The solution of compound of formula (1) was added to the mixture of DMF with phosgene at 0° C. After 14 h stirring at 0° C. and then 2 h at RT, 500 mL of water and 500 mL of toluene were added at 0° C. The mixture was stirred 30 min and the phases were separated. The organic phase was evaporated under vacuum. 54 g of compound of formula (2) were isolated (93% yield, 98.4% purity, GC analysis showed 1.1% of compound of formula (3), 0.26% of compound of formula (4) and 0.24% of compound of formula (5)).

The invention claimed is:
1. Method for the preparation of compound of formula (2)

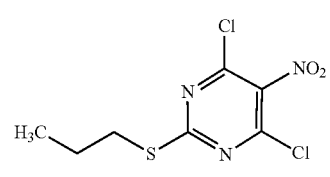

(2)

by a reaction REAC1 of compound of formula (1)

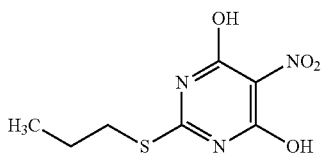
(1)

with a compound PHOS in the presence of DMF;
PHOS is selected from the group consisting of phosgene, diphosgene, triphosgene and mixtures thereof.

2. Method according to claim 1, wherein PHOS is phosgene.

3. Method according to claim 1, wherein the molar amount of PHOS is from 2 to 5 times of the molar amount of compound of formula (1).

4. Method according to claim 1, wherein the amount of DMF is from 10 to 100 times of the weight of PHOS.

5. Method according to claim 1, wherein the reaction temperature TEMPI of REAC1 is from −10 to 50° C.

6. Method according to claim 1, wherein the reaction time TIME1 of REAC1 is from 5 h to 48 h.

7. Method according to claim 1, wherein
compound of formula (1) is dissolved in DMF to provide a solution SOL-1, and PHOS is dissolved in DMF to provide a solution SOL-PHOS; and SOL-1 and SOL-PHOS are mixed with each other to provide for REAC1.

8. Method according to claim 7, wherein
for the mixing of SOL-1 with SOL-PHOS, SOL-1 is added to SOL-PHOS.

9. Method according to claim 1, wherein after REAC1 toluene and water is added to the reaction mixture.

10. Method according to claim 1, wherein the addition of toluene and water is done at a temperature of from −10 to 30° C.

* * * * *